United States Patent
Hunger et al.

(10) Patent No.: US 10,928,377 B2
(45) Date of Patent: Feb. 23, 2021

(54) MANUAL TESTING INSTRUMENT AND MANUAL TESTING METHOD FOR EXAMINING THE CONDITION OF WOOD

(75) Inventors: Erich Hunger, Karlsruhe (DE); Sebastian Hunger, Leimen (DE)

(73) Assignee: IML-INSTRUMENTA MECHANIK LABOR GMBH, Wiesloch (DE)

( * ) Notice: Subject to any disclaimer, the term of this patent is extended or adjusted under 35 U.S.C. 154(b) by 1039 days.

(21) Appl. No.: 13/642,562

(22) PCT Filed: Apr. 21, 2011

(86) PCT No.: PCT/EP2011/002039
§ 371 (c)(1),
(2), (4) Date: Jan. 2, 2013

(87) PCT Pub. No.: WO2011/131363
PCT Pub. Date: Oct. 27, 2011

(65) Prior Publication Data
US 2013/0104634 A1 May 2, 2013

(30) Foreign Application Priority Data
Apr. 23, 2010 (DE) ...................... 10 2010 018 249.4

(51) Int. Cl.
*G01N 33/46* (2006.01)
*G01N 1/08* (2006.01)
*G01N 33/00* (2006.01)

(52) U.S. Cl.
CPC ............... *G01N 33/46* (2013.01); *G01N 1/08* (2013.01); *G01N 33/0098* (2013.01)

(58) Field of Classification Search
CPC ............................ G01N 33/46; G01N 33/0098
(Continued)

(56) References Cited

U.S. PATENT DOCUMENTS

| 4,671,105 A | 6/1987 | Kamm et al. |
| 6,290,437 B1 | 9/2001 | Mattheck et al. |
| 2003/0131674 A1* | 7/2003 | Foley ........................ G01N 3/40 73/866 |

FOREIGN PATENT DOCUMENTS

| DE | 35 01 841 A1 | 7/1986 |
| DE | 40 04 242 A1 | 8/1991 |

(Continued)

OTHER PUBLICATIONS

English Translation of DE 10031395, Apr. 26, 2001.*
(Continued)

*Primary Examiner* — Alexander A Mercado
(74) *Attorney, Agent, or Firm* — Whitmyer IP Group LLC

(57) ABSTRACT

The present invention provides an instrument and a method for examining the condition of column-shaped or cylindrical sections of objects. It comprises a drive device having a drill chuck, which holds a drill needle that can be driven by the drive device, and a guiding device for guided insertion of the drill needle into the object to be examined. The guiding device is a telescopic tube that comprises a shorter inner tube section that is arranged in a longer outer tube section such that it is axially displaceable, and has a longitudinally arranged measuring scale on its outer circumference. The telescopic tube is placed on the drive device in non-rotating manner via the inner tube section. The inner and the outer tube sections have guiding means for centrally-axially guiding the drill needle, which extends in central-axial direction from the drill chuck through the inner tube section and through the outer tube section. When the inner tube section is being inserted into the outer tube section, the drill needle can be driven into the object to be examined in a manner guided by the guiding means.

20 Claims, 1 Drawing Sheet

(58) Field of Classification Search
 USPC .............................................................. 73/85
 See application file for complete search history.

(56) References Cited

FOREIGN PATENT DOCUMENTS

| DE | 41 22 494 A1 | 3/1992 | |
| DE | 4438383 A1 * | 5/1996 | ............... G01N 3/58 |
| DE | 297 07 307 U1 | 1/1998 | |
| DE | 19716817 A1 * | 11/1998 | ............... G01N 3/40 |
| DE | 100 31 395 A1 | 4/2001 | |
| DE | 102009013069 A1 * | 2/2010 | ............... G01N 3/40 |
| DE | 102011103636 A1 * | 12/2012 | |
| WO | WO 9854570 A1 * | 12/1998 | ............. G01N 33/46 |

OTHER PUBLICATIONS

English Translation of DE 4004242, Aug. 14, 1991.*
English Translation of DE 4122494, Mar. 5, 1992.*
International Search Report, PCT/EP2011/002039, dated Jan. 31, 2013, 2 pgs.

* cited by examiner

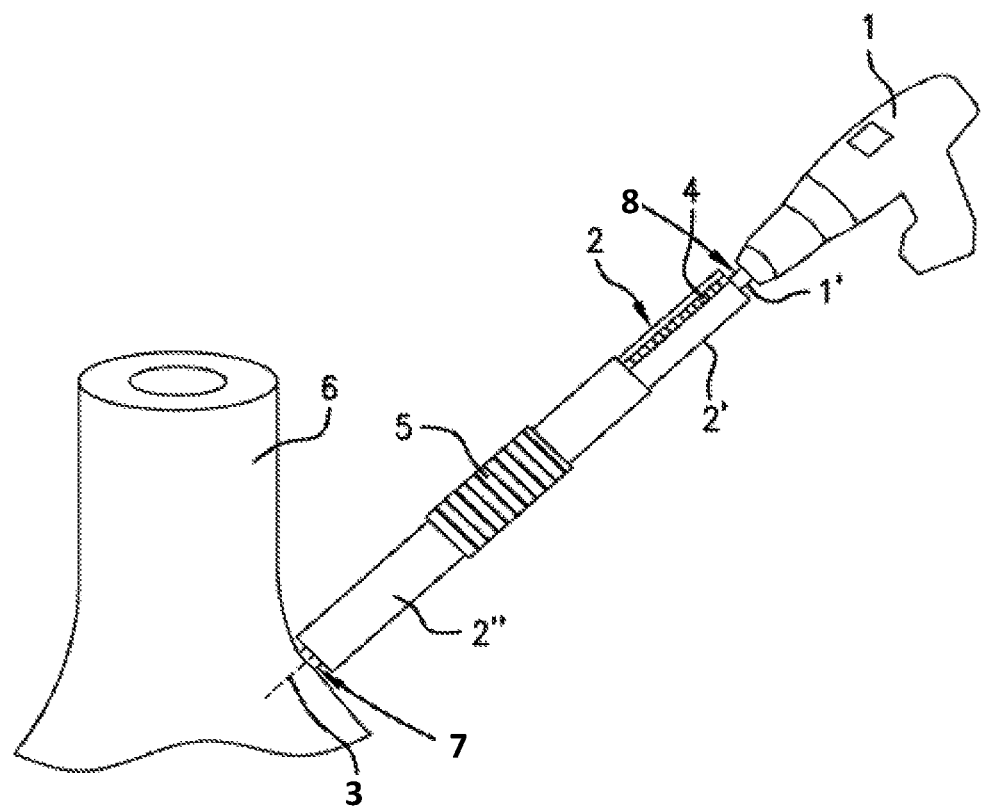

MANUAL TESTING INSTRUMENT AND MANUAL TESTING METHOD FOR EXAMINING THE CONDITION OF WOOD

CROSS-REFERENCE TO RELATED PATENT APPLICATIONS

This application is a National Stage of International Application No. PCT/EP2011/002039, filed Apr. 21, 2011, which is based upon and claims the benefit of priority from prior German Patent Application No. 10 2010 018 249.4, filed Apr. 23, 2010, the entire contents of all of which are incorporated herein by reference in their entirety.

The invention relates to a method and an instrument for examining the condition of wood and, if applicable, other column-shaped or cylindrical sections of bodies.

Methods for the testing of wood, in particular of viable wood, for investigation of its condition, are known and are mainly intended to early detect decay and other processes, for example for reasons of traffic safety.

Non-invasive methods in this context comprise the visual inspection of crown and trunk of a tree. However, developing or advanced conditions of decay inside of the trunk can usually not be detected by visual means. For this reason, it has been customary to take drill core samples to obtain samples of material from the inside of a tree, although this strongly invasive method may have a damaging effect on the tree.

In order to avoid this disadvantage, less invasive methods were developed such as the drill resistance measurement that is described in DE 3 501 841. The examination involves a drill needle being allowed to penetrate a few centimeters into the wood essentially perpendicular to the trunk axis and measuring the resistance encountered by the drill needle during its controlled insertion into the trunk. Strong deviations from an expected resistance or break-down of the mechanical resistance are indicative of a defect caused by decay or of a cavity being present. Although this method allows qualitative assessments to be made, especially when the measurement is carried out by experienced examiners, it is difficult to obtain quantitative assessments, since the drill needle is advanced evenly while it penetrates into soft material.

A device for carrying out drill resistance measurements is known from DE 10 031 395 A1, in which the drill tool drive is allowed to drive into a multiple cup telescope in order to provide better guidance of the drill. The device disclosed therein has a separate drive unit, which effects both rotation and advancement of the drill tool, perform and record the power consumption. For this purpose, a rope called advancing-pulling rope that extends through all cup bottoms of the multiple cup telescope is connected to a rotary pulse generator, for example by means of a rope-reeling mechanism, or is coupled to an optoelectronic recorder of distance markers on the rope. Accordingly, the inaccuracy of the measurement increases with the number of cup bottoms.

Another device for carrying out drill resistance measurements is known from DE 41 22 494 A1. Said device comprises a housing and a drill needle that is driven out of the housing and penetrates into the material to be examined and is advanced by means of one or two motors. The power consumption of the drill drive is detected and recorded in order to measure the density of the material while the needle, mounted on a carriage, is driven at a constant feed rate. Accordingly, the feed rate is constant even if the condition of the material changes which means that the power of the drive unit must be detected and read-out and the measured value must be correlated to the condition of the material.

DE 40 04 242 A1 also discloses a method and a device for examining cross-sections of wood: The device is designed as a simple auxiliary instrument for a common commercial battery-operated hand-held drilling machine. In this device, the tip of the needle serves as an insertion aid similar to a cork screw aiding the penetration into the material. The resistance to penetration is measured by measuring the speed while inserting the test needle.

Accordingly, based on said prior art, there is a need to generate a device that enables qualitative, and if possible quantitative, assessment of the condition of the examined bodies by minimally-invasive examination of wood, in particular of tree trunks, or other column-shaped bodies or bodies with column-shaped sections made of materials other than wood through the simplest technical design possible. The information captured in the measurement in this context should be detectable without any difficulty, preferably without having to use further reading devices.

Said object is met by a hand testing instrument having the features of independent claim 1.

Accordingly, the object is to provide an improved testing method that enables qualitative and, if possible, quantitative assessment of the condition of wood, in particular of tree trunks, or other column-shaped bodies or bodies with column-shaped sections made of materials other than wood, to be made under in situ conditions and with as little time expenditure as possible.

Said object is met by a method having the features of independent claim 7.

Preferred embodiments of the device and of the method are specified in the corresponding dependent claims.

A hand-held testing instrument according to the invention is designed for examination of the condition of column-shaped or cylindrical sections of objects. It comprises a drive device having a drill chuck, which holds a drill needle that can be driven by the drive device and is thus driven into an object. The hand-held testing instrument comprises a telescoping guiding device made up by two tube sections, whereby the inner tube section is shorter and is arranged in axially displaceable manner in a longer outer tube section. The shorter inner tube section has a longitudinally arranged measuring scale on its outer circumference.

The telescopic tube is placed directly or indirectly on the drive device in a non-rotating manner via the inner tube section. Moreover, both the inner and the outer tube sections have guide means that ensure that the drill needle can be guided centrally-axially in the telescopic tube sections. The drill needle can be fixed in place in the drill chuck by means of a clamping screw; alternatively, fastening can be provided by means of a thread being situated on the outside of the drill needle.

The drill needle extends in central-axial direction from the drill chuck through the inner tube section to the outer tube section from which it either projects or with which it ends such as to be flush. The drill needle is guided in the tube sections of the telescopic tube, where it is arranged in such manner that it can be driven into the object to be examined in guided manner guided in the external tube section by the guiding means when the inner tube section is being inserted (in the use position), which is combined with manual advancement of the drive device on which the inner tube section is situated.

Thus, according to the invention a testing instrument is provided that is easy to handle and comprises neither an electronic nor a mechanical recorder.

Just the resistance to axial penetration of the rotating drill needle is recorded during operation of the device, whereas the torsion power is not measured.

Although the hand-held testing instrument according to the invention comprises a drill needle that is guided on the inside and is driven by a drive unit much alike the one of a drilling machine, the needle is not advanced at a constant rate, which is done by hand by means of the two guide tubes. Depending on the structure, the feed rate can vary depending on the properties of the material. Due to this procedure being used, the user is allowed, directly and without needing any further devices, to recognize differences in the material and assess them by simply reading the measuring scale.

In general, hard material requires a higher contact force of the device against the material to be examined as compared to soft material; hollow spaces do not require contact force at all. Thus, the hand-held testing instrument according to the invention introduces the needle into the material by means of a constant pressure and the differences in torque are detected as a function of the drilling depth.

Detecting a cavity in the material, the machine can advantageously be switched off after drilling through the residual wall, and the residual wall thickness can be read on the scale and thus measured while the needle is in stationary mode and being retracted. The needle head being thicker allows a clear difference between hollow space and drill channel to be recognized in a simple manner.

The needle guidance of the hand-held testing instrument can be implemented by means of the telescopic tubes with inside guide sleeves; the needle is fixed in place in the drill chuck by means of a clamping screw. Alternatively, fastening can just as well involve an external thread being present on the drill needle.

Another alternative embodiment providing for guidance can be obtained by means of guiding means that are situated on the ends of the inner and outer tube sections facing away from the drive device. Sleeves can be used for this purpose. A sleeve on the longer outer tube section can comprise a spiral internal thread whose shape corresponds to an external thread that is present on the needle.

Advantageously, the shorter inner tube section of the telescopic tube through which the same contacts the drive means is connected to the drive means in non-rotating manner by means of a simple sleeve; a sleeve of this type can simply be plugged on. It serves as a spacer and will usually have an internal diameter that is adapted to the external diameter of the drill needle.

For comfortable handling of the hand-held testing instrument according to the invention, the instrument can comprise a handle sleeve about the external circumference of its outer tube section. Handling a handle sleeve of this type is particularly comfortable if the handle sleeve is made of an elastic material. The handle sleeve helps with guiding and supporting the telescopic tube.

Moreover, the measuring scale that is present on the inner tube section and can extend over the entire length of the inner tube section, but is present at least on the longitudinal section facing the drive means, is equipped with a scale for reading the inserted length of the inner tube section in the outer tube section in units of millimeters, inches, "Zoll" or centimeters.

Accordingly, the hand-held testing instrument can be used to implement a testing method for examining the condition of column-shaped or cylindrical sections of objects that comprises, initially, pulling the inner out of the outer telescope tube followed by placing the needle, which projects from the outer tube section and is guided by the guide means, on the object to be examfined. Said object can be a tree, although dead wood or other materials can be examined just as well.

Then the drive means is activated and the needle begins to rotate. This drives the needle into the object which results in a first resistance that is due to the material of the object and needs to be overcome by the needle being driven into said object. Due to the needle being driven into the object, the hand-held drive means is advanced axially in the direction of the object and inserts the inner tube section of the telescopic tube into the outer tube section. If the needle is used for examining a tree, the resistance to axial penetration of the rotating needle changes abruptly, i.e. in non-steady manner.

Said change of resistance is noticed by the user directly and clearly; at the same time the inserted length of the inner tube section in the outer tube section is read. This provides a direct measure of how far the needle penetrated through healthy wood with a higher resistance to penetration before encountering the soft decaying wood.

The hand-held testing instrument is easy to transport and simple in design such that it can be operated by anybody and requires no complicated installation at an object to be examined, which predominantly will be wood, in particular viable trees, which are often a hazard in urban areas if they are decaying and are situated near roads.

Accordingly, the hand-held testing instrument according to the invention is an advantageous means for rapid and inexpensive examination of a large number of trees and wood constructions as well as wooded poles for the presence of decay, and thus makes a contribution to road safety.

Further embodiments as well as some of the advantages that are associated with these and further embodiments are made clear and more comprehensible by the detailed description provided in the following. This is supported by the description referring to the FIGURE.

FIG. 1 shows a side view of a hand-held testing device according to the invention.

FIG. 1 shows a hand-held testing device according to the invention that can be used to examine wood, wooden poles, in particular viable wood, or trees for their condition which is expressed, for example, in changes of the density and chemical composition thereof. The term, "condition", shall be clarified by means of an example: A cross-section of a tree trunk basically shows the well-known (annual) tree rings that are generated while the tree ages and can differ in the composition, structure, and water content of their wood fibres, but, in the case of diseased wood, can comprise decomposed and decomposing sections whose composition can also contain fungi and their decomposition products—to name just one component for exemplary purposes.

The device has no recorder, neither an electronic nor a mechanical recorder, but solely measures the resistance to axial penetration of a rotating needle penetrating into the object. A torsional power is not being captured. The axial force required for this purpose is felt by hand by the user.

To make this simple and safe to execute by any user, the hand-held testing device is designed as shown in FIG. 1: It comprises a drive means 1, which can be a common commercial drilling machine 1. The drive means has a drill chuck into which a drill needle 3 can be inserted. The drill needle is driven by the drive means. Moreover, the hand-held testing device comprises a guidance device 2 for guided penetration of the drill needle 3 into the object 6 to be examined, in the present case a tree trunk, and a reading device 4 that shows the depth at which the diseased wood can be detected.

The guidance device 2 is a telescopic tube that comprises an inner tube section 2' that is shorter than the outer tube section 2" surrounding it. The inner tube section 2' is arranged in the outer tube section 2" in axially displaceable manner and comprises a measuring scale 4. The measuring scale 4 indicates the drilling depth in units of centimeter, "Zoll", inch, and millimeter scaling.

As is shown, the drill needle 3, which has already penetrated into the object 6 in the present case, is guided at the outer tube section 2" by guiding means 7. In the present case, the needle is guided by the telescopic tubes having internal guide sleeves 7 and the needle is fixed in place in the drill chuck by means of a clamping screw 8'. In other embodiments, the guiding means 7 can be guide bushings 7-1, sleeves 7-2, and/or sleeves having internal thread 7-3.

This ensures that the needle is guided centrally-axially from the drill chuck of the drive means 1 to its exit from the outer tube section 2". The inner tube section 2', not shown in the FIGURE, can also comprise guiding means at its end facing away from the drilling machine 1.

The sleeves serving as guiding means can be encased in a closing lid that can be placed on the inner and the outer tube sections each. Moreover, the inner tube section can be designed to be nearly solid and comprise on its inside just a longitudinal bore hole with an internal diameter that is just larger than the external diameter of the needle. The guiding means of the outer tube section that directly contacts the tree can be provided with a spiral thread that is matched in its shape to the spiral thread of the needle.

Moreover, the hand-held testing device according to the invention comprises a handle sleeve 5 that allows one hand to be placed safely and comfortably on the outer telescope tube in order to guide and support the outer telescope tube, as shown in FIG. 1.

Accordingly, a measurement can be carried out to detect decay in a tree by placing the outer tube section of the telescopic tube against a tree by means of its exit opening for the needle, whereby the inner tube section is present in pulled-out condition at the start of the measurement. Then the drilling machine is turned on and the needle begins to rotate. In this context, the drilling machine and the inner tube section, which is placed against the drill chuck of the drive means in non-rotating manner by means of a spacer sleeve, are pushed into the outer tube section.

A resistance to penetration from the healthy wood needs to be overcome in the process. The procedure is analogous when objects other than trees are measured. As soon as the composition of the material, and thus the resistance to penetration, changes, the needle performs a jerky motion and penetrates more deeply into the wood or the material of the object to be examined. Even (annual) tree rings of coniferous trees can be noticed by some "jerking" in the examination of trees. Exactly at the point in time, at which the resistance to penetration changes in a non-steady manner, the measuring scale on the inner tube section can be read to indicate how far the inner tube section could be inserted into the outer tube section at the earlier resistance to penetration.

Accordingly, the examination of wood allows to determine which section of the wood is healthy and thus shows the higher resistance to penetration, which is usually detected first. As a matter of principle, this provides easy means for anybody to determine whether or not decay is evident on the inside of the tree or wood. Accordingly, the hand-held testing instrument according to the invention supplements visual tree inspections and provides a simple and inexpensive examination and can thus contribute to early detection of diseased trees and preventing a diseased tree from causing damage. It is advantageous that the method according to the invention is only minimally invasive meaning that the body, which may be a trunk of a viable tree or a column made of concrete, is damaged only in that a drill needle is inserted into the body, whereas no substantial amount of material is removed such that any weakening of the material or damage at the examination site is minimized. And still, in addition to the qualitative assessment of whether or not decay is present, a quantitative assessment is made with regard to the depth at which the decaying layer is situated and possibly even of its extent.

The invention claimed is:

1. A hand-held testing instrument for examining the condition of column-shaped or cylindrical sections of an object, comprising:
a drive device having a drill chuck, which holds a drill needle that is driven by the drive device;
a guiding device for centrally-axially guiding the drill needle into the object to be examined, wherein the guiding device comprises a telescopic tube;
wherein said telescopic tube comprises two tube sections including a shorter inner tube section and a longer outer tube section, wherein the shorter inner tube section is arranged in the longer outer tube section such that it is axially displaceable and has a longitudinally arranged measuring scale on an outer circumference of the inner tube section;
wherein said telescopic tube is mounted on the drive device via the inner tube section in non-rotating manner, wherein the drive device is a drilling machine;
wherein the drill needle extends in a central-axial direction from the drill chuck such that the drill needle and the drill chuck are co-axially aligned relative to one another;
wherein the drill needle extends through the inner tube section and through the outer tube section;
wherein the drill needle is configured to be driven into the object to be examined in a manner guided by the guiding device while the inner tube section is being inserted into the outer tube section;
wherein the hand-held testing instrument comprises neither an electronic nor a mechanical recorder, wherein the longitudinally arranged measuring scale on the outer circumference of the inner tube section provides a direct measure of how far the needle penetrated the object.

2. The hand-held testing instrument according to claim 1, wherein the guiding device further comprises a structure selected from the group consisting of guide bushings situated in the inner tube section, the outer tube section, or sleeves.

3. The hand-held testing instrument according to claim 1, further comprising a sleeve that is connected to the inner tube section which is imposed in a non-rotating manner on the drill chuck of the drive device.

4. The hand-held testing instrument according to claim 1, further comprising a handle sleeve around an external circumference of the outer tube section which is arranged to guide and support the handling of the telescopic tube.

5. The hand-held testing instrument according to claim 1, wherein the longitudinally arranged measuring scale comprises a scale in units of millimeters or centimeters for reading an inserted length of the inner tube section in the outer tube section.

6. The hand-held testing instrument according to claim 1, wherein the drill needle is fixed in place in the drill chuck by using a clamping screw.

7. A method for examining the condition of column-shaped or cylindrical sections of an object using the hand-held testing instrument according to claim 1, comprising the steps of:
provinding the telescopic tube;
wherein the shorter inner tube section is in a pulled-out state;
placing the drill needle, which projects from the outer tube section in a manner guided by the guiding device, on the object to be examined;
actuating the drive device and driving the drill needle in a rotary manner and driving the drill needle into the object against a first resistance given by the object;
axially displacing the drive device by hand in the direction of the object and thus inserting the inner tube section into the outer tube section;
reading an inserted length of the inner tube section in the outer tube section as soon as a resistance provided by the object changes.

8. The hand-held testing instrument according to claim 2, further comprising a sleeve that is connected to the inner tube section which is imposed in a non-rotating manner on the drill chuck of the drive device.

9. The hand-held testing instrument according to claim 2, further comprising a handle sleeve around an external circumference of the outer tube section which is arranged to guide and support the handling of the telescopic tube.

10. The hand-held testing instrument according to claim 2, wherein the longitudinally arranged measuring scale comprises a scale in units of millimeters or centimeters allowing the reading of an inserted length of the inner tube section in the outer tube section.

11. The hand-held testing instrument according to claim 2, wherein the drill needle is fixed in place in the drill chuck by using a clamping screw.

12. A method for examining the condition of column-shaped or cylindrical sections of an object using the hand-held testing instrument according to claim 2, comprising the steps of:
providing the telescopic tube, wherein the shorter inner tube section is in a pulled-out state;
placing the drill needle, which projects from the outer tube section in a manner guided by the guiding device, on the object to be examined;
actuating the drive device and driving the drill needle in a rotary manner and driving the drill needle into the object against a first resistance given by the object;
axially displacing the drive device by hand in the direction of the object and thus inserting the inner tube section into the outer tube section;
reading an inserted length of the inner tube section in the outer tube section as soon as a resistance provided by the object changes.

13. The hand-held testing instrument according to claim 9, further comprising a handle sleeve around an external circumference of the outer tube section which is arranged to guide and support the handling of the telescopic tube.

14. The hand-held testing instrument according to claim 9, wherein the longitudinally arranged measuring scale comprises a scale in units of millimeters or centimeters allowing the reading of an inserted length of the inner tube section in the outer tube section.

15. The hand-held testing instrument according to claim 9, wherein the drill needle is fixed in place in the drill chuck by using a clamping screw.

16. A method for examining the condition of column-shaped or cylindrical sections of an object using the hand-held testing instrument according to claim 9, comprising the steps of:
providing the telescopic tube, wherein the shorter inner tube section is in a pulled-out state;
placing the drill needle, which projects from the outer tube section in a manner guided by the guiding device, on the object to be examined;
actuating the drive device and driving the drill needle in a rotary manner and driving the drill needle into the object against a first resistance given by the object;
axially displacing the drive device by hand in the direction of the object and thus inserting the inner tube section into the outer tube section;
reading an inserted length of the inner tube section in the outer tube section as soon as a resistance provided by the object changes.

17. The hand-held testing instrument according to claim 13, wherein the longitudinally arranged measuring scale comprises a scale in units of millimeters or centimeters for reading an inserted length of the inner tube section in the outer tube section.

18. The hand-held testing instrument according to claim 13, wherein the drill needle is fixed in place in the drill chuck by using a clamping screw.

19. A method for examining the condition of column-shaped or cylindrical sections of an object using the hand-held testing instrument according to claim 13, comprising the steps of:
providing the telescopic tube, wherein the shorter inner tube section is in a pulled-out state;
placing the drill needle, which projects from the outer tube section in a manner guided by the guiding device, on the object to be examined;
actuating the drive device and driving the drill needle in a rotary manner and driving the drill needle into the object against a first resistance given by the object;
axially displacing the drive device by hand in the direction of the object and thus inserting the inner tube section into the outer tube section;
reading an inserted length of the inner tube section in the outer tube section as soon as a resistance provided by the object changes.

20. A hand-held testing instrument for examining the condition of column-shaped or cylindrical sections of an object, comprising:
a drive device having a drill chuck, which holds a drill needle that is driven by the drive device;
a guiding device for centrally-axially guiding the drill needle into the object to be examined, wherein the guiding device comprises a telescopic tube;
wherein said telescopic tube comprises two tube sections including a shorter inner tube section and a longer outer tube section, wherein the shorter inner tube section is arranged in the longer outer tube section such that it is axially displaceable and has a longitudinally arranged measuring scale on an outer circumference of the inner tube section;
wherein the inner and outer tube sections comprise guide bushings and sleeves for guiding the drill needle in the telescopic tube in a centrally axial manner, wherein the sleeves are arranged at an end of each of the shorter and longer tubes facing away from the drive device;

wherein said telescopic tube is mounted on the drive device via the inner tube section in non-rotating manner, wherein the drive device is a drilling machine;

wherein the drill needle extends in a central-axial direction from the drill chuck such that the drill needle and the drill chuck are co-axially aligned relative to one another;

wherein the drill needle extends through the inner tube section and through the outer tube section;

wherein the drill needle is configured to be driven into the object to be examined in a manner guided by the guiding device while the inner tube section is being inserted into the outer tube section;

wherein the longitudinally arranged measuring scale on the outer circumference of the inner tube section is arranged to have the outer tube section cover the longitudinally arranged measuring scale in direct proportion to how far the needle penetrated the object.

\* \* \* \* \*